(12) United States Patent
Chang et al.

(10) Patent No.: US 9,228,974 B2
(45) Date of Patent: *Jan. 5, 2016

(54) BIOSENSING WELL ARRAY BY SELF-ALIGNMENT AND SELECTIVE ETCHING

(71) Applicant: Taiwan Semiconductor Manufacturing Company, Ltd., Hsin-Chu (TW)

(72) Inventors: Yi-Hsien Chang, Shetou Township (TW); Wei-Cheng Shen, Tainan (TW); Shih-Wei Lin, Taipei (TW); Chun-Ren Cheng, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 49 days.

This patent is subject to a terminal disclaimer.

(21) Appl. No.: 13/946,782

(22) Filed: Jul. 19, 2013

(65) Prior Publication Data

US 2014/0308752 A1 Oct. 16, 2014

Related U.S. Application Data

(60) Provisional application No. 61/810,658, filed on Apr. 10, 2013.

(51) Int. Cl.
*G01N 27/414* (2006.01)

(52) U.S. Cl.
CPC ... *G01N 27/4145* (2013.01); *Y10T 436/143333* (2015.01)

(58) Field of Classification Search
None
See application file for complete search history.

(56) References Cited

U.S. PATENT DOCUMENTS

2012/0045368 A1* 2/2012 Hinz et al. ............... 422/69

FOREIGN PATENT DOCUMENTS

WO WO2012152308 * 11/2012

* cited by examiner

*Primary Examiner* — Melanie Y Brown
*Assistant Examiner* — Rebecca Martinez
(74) *Attorney, Agent, or Firm* — Slater & Matsil, L.L.P.

(57) ABSTRACT

The present disclosure provides a biological field effect transistor (BioFET) and a method of fabricating a BioFET device. The method includes forming a BioFET using one or more process steps compatible with or typical to a complementary metal-oxide-semiconductor (CMOS) process. The BioFET device includes a plurality of microwells having a bio-sensing layer and a number of stacked well portions over a multi-layer interconnect (MLI). A bottom surface area of a well portion is different from a top surface area of a well portion directly below. The microwells are formed by removing a top metal plate on a topmost level of the MLI.

20 Claims, 12 Drawing Sheets

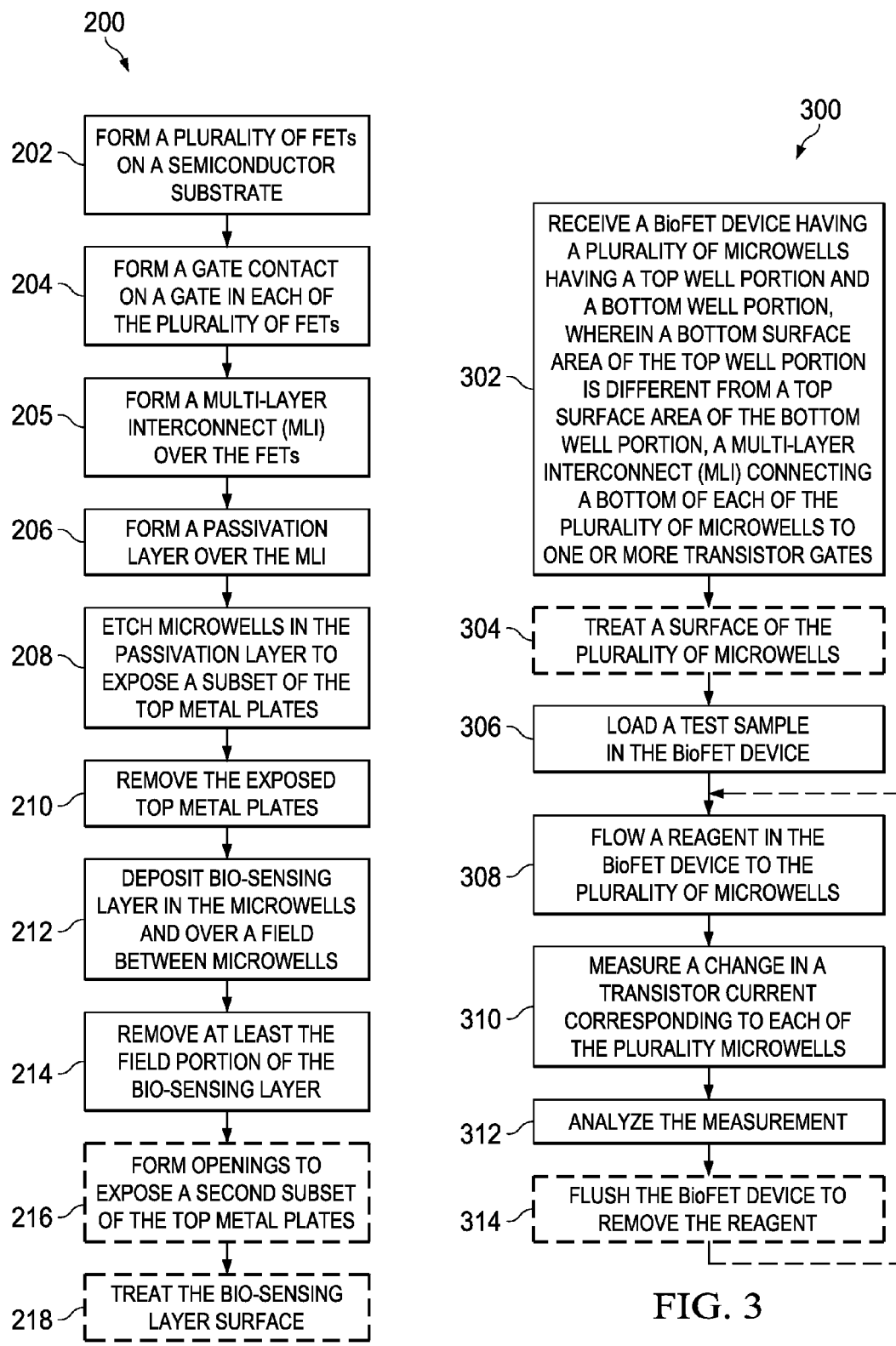

BIOSENSING WELL ARRAY BY SELF-ALIGNMENT AND SELECTIVE ETCHING

This application claims priority to U.S. Provisional Application Ser. No. 61/810,658, filed on Apr. 10, 2013, entitled "Biosensing Well Array by Self-Alignment and Selective Etching," which application is hereby incorporated herein by reference.

FIELD

This disclosure relates to biosensors and methods for forming biosensors. Particularly, this disclosure relates to biological field-effect-transistors (bioFETs) and methods for forming them.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and microelectromechanical systems (MEMS).

Biochips are essentially miniaturized laboratories that can perform hundreds or thousands of simultaneous biochemical reactions. Biochips can detect particular biomolecules, measure their properties, process the signal, and may even analyze the data directly. Biochips enable researchers to quickly screen large numbers of biological analytes in small quantities for a variety of purposes, from disease diagnosis to detection of bioterrorism agents. Advanced biochips use a number of biosensors along with microfluidics to integrate reaction, sensing and sample management. BioFETs (biological field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, sensitivity and resolution of the electrical signals and biological applications, and/or other challenges arising from implementing a large scale integration (LSI) process.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 2 is a flow chart of an embodiment of a method of fabricating a BioFET device according to one or more aspects of the present disclosure.

FIG. 3 is a flow chart of an embodiment of a method of using a BioFET device according to one or more aspects of the present disclosure.

DETAILED DESCRIPTION

Figure 1:
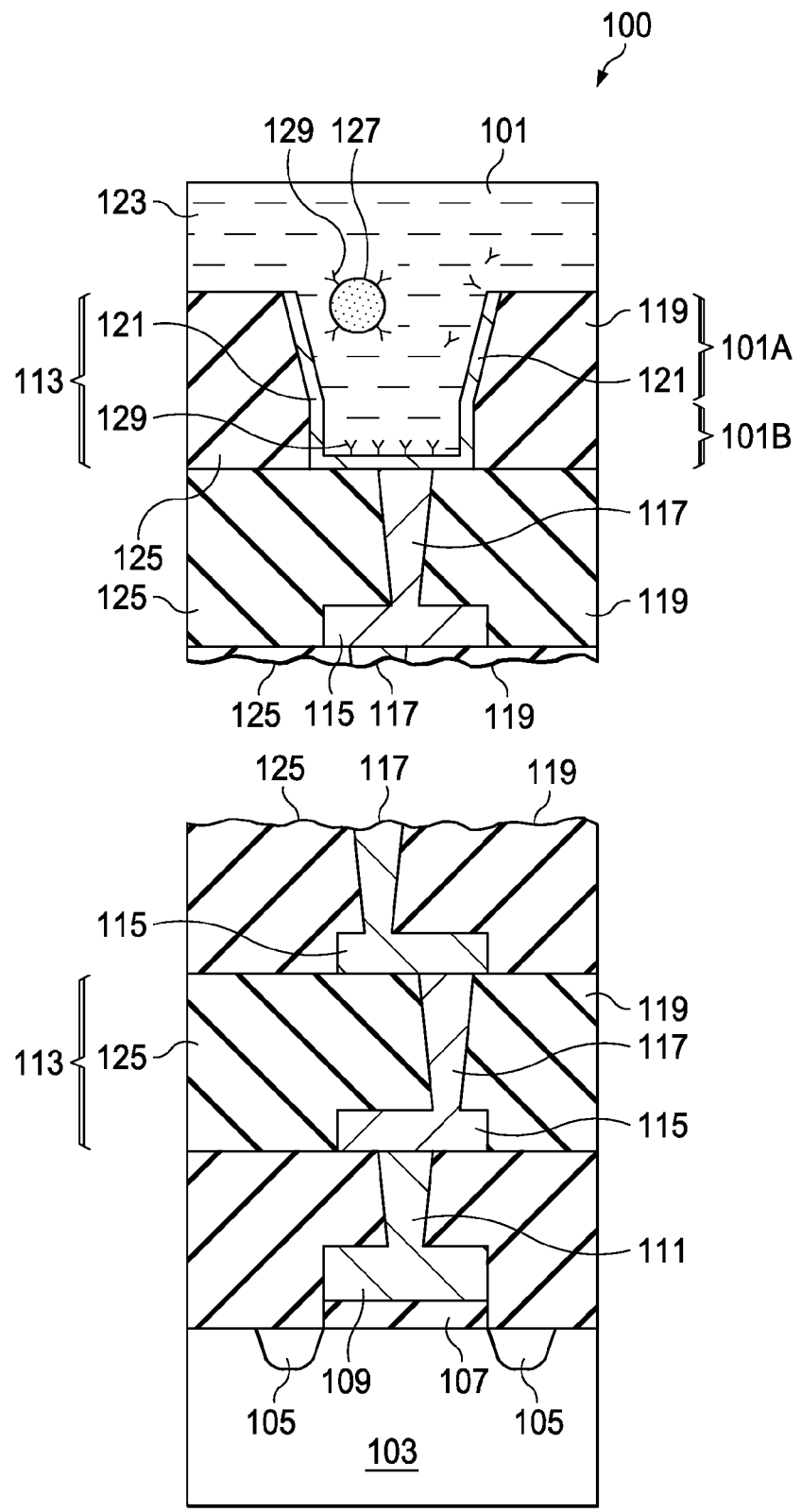
FIG. 1 is a cross-sectional view of a BioFET according to one or more embodiments in accordance with the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a biological field-effect transistor (BioFET), the gate of a metal-oxide-semiconductor field-effect transistor (MOSFET), which controls the conductance of the semiconductor between its source and drain contacts, includes a bio- or biochemical-compatible layer or a biofunctionalized layer of immobilized probe molecules that act as surface receptors. Essentially, a BioFET is a field-effect biosensor with a semiconductor transducer. An advantage of BioFETs is the label-free operation. Specifically, using BioFETs can avoid costly and time-consuming labeling operations such as the labeling of an analyte with, for instance, fluorescent or radioactive probes.

Binding of a target biomolecule or bio-entity to the gate or a receptor molecule immobilized on the gate of the BioFET modulates the conductance of the BioFET. When the target biomolecule or bio-entity is bonded to the gate or the immobilized receptor connected to the gate, the drain current of the BioFET is varied by the gate potential, which depends on the type and amount of target bound. This change in the drain current can be measured and used to determine the type and amount of the bonding between the receptor and the target biomolecule or the biomolecule itself. In some embodiments of different circuit design, the device could work in linear or saturation region of the IV curve for biosensing. A variety of receptors may be used to functionalize the gate of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the gate of the BioFET may be functionalized with immobilized complementary ssDNA strands.

Also, to detect various proteins such as tumor markers, the gate of the BioFET may be functionalized with monoclonal antibodies.

One example of a biosensor has a sensing surface as a top of a metal plate connected to the gate of the BioFET. The metal plate and the sensing surface is a floating gate for the BioFET. The floating gate is connected to the gate structure of the BioFET through a stack of metal interconnect lines and vias (or multi-layer interconnect, MLI). In such a BioFET, the potential-modulating reaction takes place at an outer surface of the metal plate or a dielectric surface formed on top of the metal plate. The top metal layer includes a number of metal plates each connected to a different transistor. A microwell is formed over the top metal layer for each BioFET. The microwells are isolated from each other and each includes a bio-sensing layer on which the reactions take place. The various microwells are connected by microfluidic channels. Reagents are flowed through the microfluidic channels to each bio-sensing layer in the microwells. The reagents include test samples that may directly bind to the bio-sensing layer or indirectly through a carrier. An example of a carrier is a bead having the test samples bound thereon. In one example, the binding reaction changes a local ion concentration (pH) in a microwell that causes a change in the internal charge of the bio-sensing layer. The charge of the bio-sensing layer is transmitted to the transistor gate through the various metal layers as a voltage signal. The change in gate voltage changes the amount of current flowing between the source and drain of the BioFET. By detecting the current, the change in pH in the microwell is measured. Size of the microwells is directly related to the signal intensity. Larger microwells allow a larger bio-sensing layer/more bio-entities that can include more binding sites to create a stronger signal. However, if the top metal plate is exposed to the analyte, the top metal electrode may corrode and render the BioFET defective. To ensure that the top metal plate is not exposed to the analyte, a bottom of the microwell is sized to be smaller than the top surface of the top metal plate within alignment tolerances. In other words, the bottom of the microwell is sufficiently small such that even with misalignment, the microwell would still be situated over the metal plate. Further, adequate spacing must be maintained between adjacent top metal plates to isolate the microwells from each other as well as following the design rules for the top metal electrodes.

An increase in biochip capacity is desirable to allow more simultaneous reactions and more accurate measurements. Higher biochip capacity involves building more transistors and a higher number of corresponding microwells. Having more microwells reduces the area of each microwell, as only a finite space is available on the biochip. When the size of the microwells decreases, the area of the bio-sensing layer also decreases, which decreases signal intensity and increases signal-to-noise ratio (SNR).

One way to minimize the decrease in signal intensity involves preserving the bio-sensing layer area as the number of microwells increase. In some examples, microwells having bottoms larger than the top metal plate are used. The larger microwell bottom increases the bio-sensing layer area. While the microwells are larger, a gap between the top metal plate and the passivation wall may be created that are filled by the bio-sensing layer. A misalignment between the microwell and the top metal plate can create a crack corrosion site and render the transistor defective. With metal bio-sensing layers, the likelihood that the bio-sensing layer bridges to the top metal of an adjacent microwell increases when there is a misalignment. Therefore, having microwells with bottoms larger than the top metal makes misalignment window very small for the microwell and top metal electrode.

Other examples to increase the bio-sensing layer area involves adding a smaller metal plug over the top metal electrode and a sensing plate over the smaller metal plug. The sensing plates may be placed closer than the top metal plates and thereby increase the area of the microwells. Having a sensing plate over the smaller metal plug reduces the likelihood of bridging signals between adjacent microwells. However, adding a smaller metal plug and a sensing plate having different dimensions adds two additional layers with two photomask patterns that increase the manufacturing cost significantly.

The present disclosure pertains to a method and structure for forming microwells that is larger as compared to the microwells over the top metal plates without misalignment issues. The microwells may be the same or smaller than the microwells having a bottom larger than the metal plates, but without increasing the likelihood of bridging signals and with only one additional photomask. According to various embodiments, the top metal electrode is removed in a selective etching process before the bio-sensing layer is deposited. The selective etching process creates self-aligned microwells without affecting the alignment tolerance window. A bio-sensing layer is deposited in the microwells and over the field. At least the field portion of the bio-sensing layer is removed in an etch process while a photomask protects the portions of the bio-sensing layer within the microwells. The removal of the field portion of the bio-sensing layer isolates the microwells from each other.

FIG. 1 is a cross-sectional view of a BioFET 100 according to one or more embodiments in accordance with the present disclosure. The BioFET 100 includes a substrate 103 on and in which a transistor is formed. The source and drain regions 105 are formed in the substrate 103. A gate stack including gate dielectric 107 and gate electrode 109 is formed on the substrate 103. As shown in FIG. 1, the transistor in BioFET 100 is a planar transistor; however, other types of transistors may be used, including a multi-gate transistor or a FinFET. The BioFET 100 also includes a gate contact 111 over the gate electrode 109. Contacts to the source and the drain (not shown) are also included. A number of metal interconnect layers 113 interpose between the gate contact 111 and a microwell 101. Each metal interconnect layer 113 includes a metal line 115 and metal via 117 within a layer of intermetal dielectric 119. Three metal interconnect layers 113 are shown, but fewer or more may be used.

The microwell 101 is an opening in the passivation layer 125 and includes a top portion 101A and a bottom portion 101B. Sidewalls of the microwell 101 have at least one step, shelf, or corner between the top and bottom portions 101A and 101B. In other words, a bottom surface area of the top portion is different from a top surface area of the bottom portion. For the microwell 101, the bottom surface area of the top portion 101A is larger than a top surface area of the bottom portion 101B. The bottom surface area of the bottom portion may be the same or larger than the bottom surface area of the top portion.

The microwell 101 includes a bio-sensing layer 121 on the bottom and at least a portion of the sidewalls. Having bio-sensing layer 121 on the sidewalls increases the surface area of the bio-sensing layer 121. According to various embodiments, the sidewalls may not be fully covered by the bio-sensing layer 121. The bio-sensing layer 121 may be a metal, dielectric, or a polymer. Examples include titanium nitride, high-k dielectric such as aluminum oxide, lanthanum oxide, hafnium oxide, and tantalum oxide, self-assembled monolayer, or hydrogel.

The microwell 101 may include one or more layers under the bio-sensing layer 121 at the bottom of the microwell. The one or more layers may be an adhesion layer, an etch stop layer, or an anti-reflection coating. Examples of an adhesion layer or an etch stop layer include titanium nitride, titanium, titanium tungsten or germanium. The anti-reflection coating may be silicon oxynitride or other commonly used dielectric. There is no anti-reflection coating where the metal via 117 contacts the bottom of the microwell 101.

A BioFET device includes a number of BioFETs 100 with microwells 101 that are in fluidic communication with each other. Each microwell 101 is associated with gates of one or more transistors. When a microwell 101 is connected to the gates of more than one transistor, a higher frequency sampling may be performed to increase the accuracy of the measurement. The microwells are connected by microfluidic channels forming an array of bioFETs 100. The microfluidic channels allow analyte 123 to flow from an inlet of the BioFET device to an outlet of the BioFET device. The microfluidic channels may be above the microwells 101 as shown in FIG. 1 or be at a same level as the microwells 101. The analyte 123 includes test samples and a carrier medium. In some embodiments, the test samples include functionalized beads 127 on which specific biomolecules 129 from the test samples would bind. The functionalized beads are sized such that only a particular numbers of them would fit in a microwell. For example, the functionalized beads 127 may be slightly smaller than a microwell such that only one bead 127 can fit in a microwell. The biomolecules 129 on the functionalized bead 127 would change the fluidic in the microwell 101 in a way that is detectable by the transistor. In other embodiments, the test sample includes biomolecules 129 that would bind to receptors (not shown) labeled on the bio-sensing layer 121 without using carrier beads. For example, single stranded deoxyribonucleic acid (ssDNA) is bound on the sensing layer and amplified with PCR (polymarse chain reaction) to duplicate the same DNA to increase sites. Then, reagent is flowed through the microwells for DNA sequencing. Other examples include protein labeling and anti-body/anti-gen reactions.

FIG. 2 is a method 200 of fabricating a BioFET device according to one or more aspects of the present disclosure. The method 200 begins at operation 202 where a plurality of field-effect transistors (FETs) are formed on a semiconductor substrate. The semiconductor substrate may be a silicon substrate. Alternatively, the substrate may include another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the substrate is a semiconductor on insulator (SOI) substrate. The SOI substrate may include a buried oxide (BOX) layer formed by a process such as separation by implanted oxygen (SIMOX), and/or other suitable processes. The substrate may include doped regions, such as p-wells and n-wells. In the present disclosure, a wafer is a semiconductor substrate and various features formed in and over the semiconductor substrate. The wafer may be in various stages of fabrication and is processed using the CMOS process.

In operation 204, a gate contact is formed on a gate in each of the FETs. The gate contacts are formed in typical CMOS processing. Contacts are also formed over and physically connecting to the source/drain regions. In operation 206 a multi-layer interconnect (MLI) is formed over the FETs. The MLI structure may include conductive lines, conductive vias, and/or interposing dielectric layers (e.g., interlayer dielectric (ILD)). The MLI structure provides electrical connection to the transistor. The conductive lines in various levels may comprise copper, aluminum, tungsten, tantalum, titanium, nickel, cobalt, metal silicide, metal nitride, poly silicon, combinations thereof, and/or other materials possibly including one or more layers or linings. The linings include adhesion layer, barrier layer, etch stop layer, and anti-reflective coatings. The interposing or inter-layer dielectric layers (e.g., ILD layer(s)) may comprise silicon dioxide, fluorinated silicon glass (FSG), SILK (a product of Dow Chemical of Michigan), BLACK DIAMOND™ (a product of Applied Materials of Santa Clara, California), and/or other insulating materials. The MLI may be formed by suitable processes typical in CMOS fabrication such as CVD, PVD, ALD, plating, spin-on coating, and/or other processes.

The number of metal layers in the MLI depends on routing needs for the FETs. For simple BioFET devices where little or no analysis and processing are performed on the device, fewer metal layers are used, for example, 3 metal layers. In some embodiments, the BioFET devices process or analyze the measurements, more metal layers are used, for example, four, five, or eight metal layers. The use of more metal layers allows more transistors to be used on the device that can perform complex logic operations with or without additional external input. Further, the results from the BioFETs can be used as input that triggers further device operations. In one example, the further device operation may flow the contents of a microwell toward a more sensitive BioFET or a BioFET where a chemical reaction would break up some of the biological content. With additional processing power, a lab-on-a-chip type of device is formed where the output from the device includes results of the analysis instead of only raw data. For example, the device may determine whether a blood sample contains cancer cells, quantify the cancer cells, and output a cancer type. In another example, the device may determine a genetic sequence.

A topmost layer of the MLI is the top metal layer that includes a number of metal plates. The metal plates may include aluminum, copper, or tungsten. Some metal plates are each individually connected to the gate contact of a BioFET. Other metal plates are used for signal transmission, such as bonding pads for bonding wires or bumps.

Figure 4:
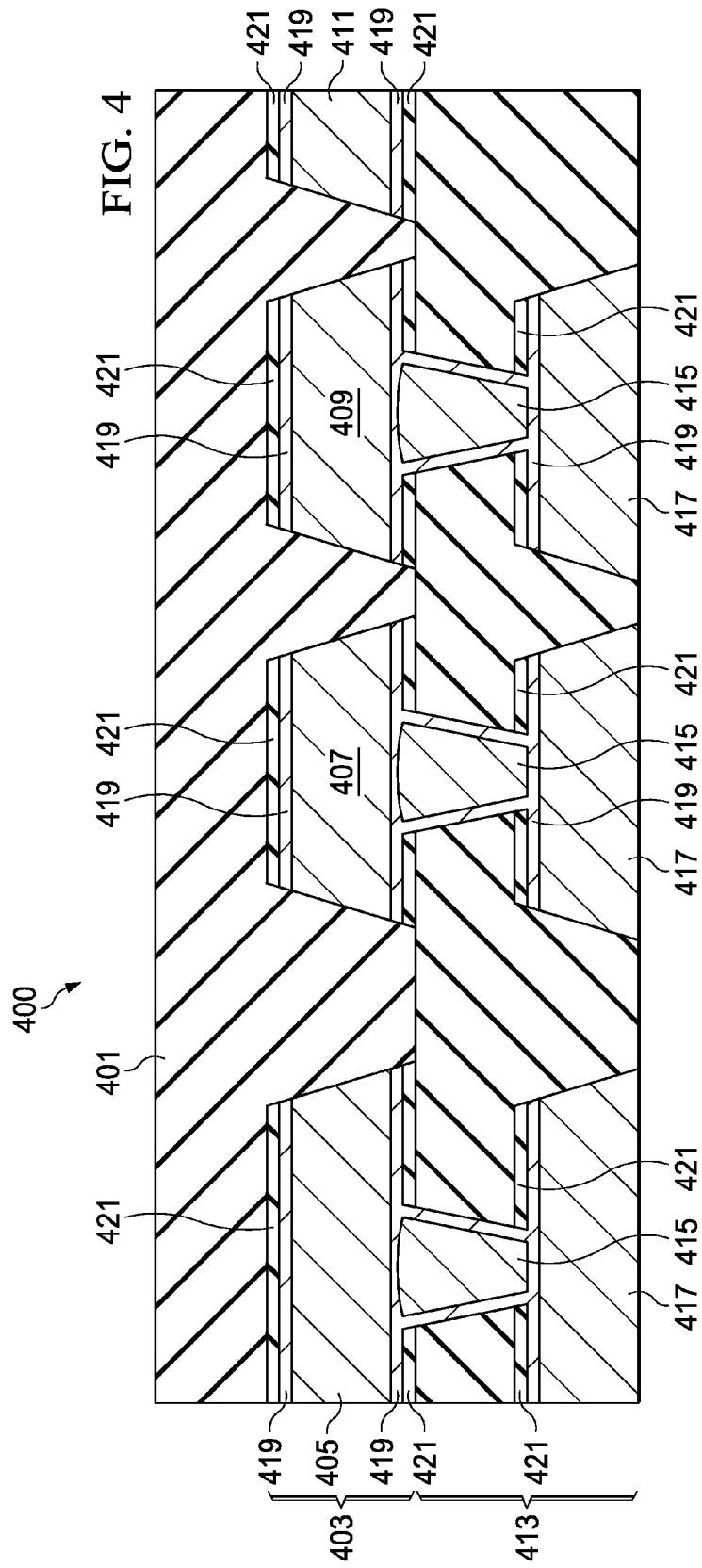
FIGS. 4 to 9 are cross-sectional views of a BioFET device at various intermediate stages of formation according to one or more aspects of the present disclosure.

In operation 206, a passivation layer is formed over the MLI. The passivation layer is deposited over the top metal layer. The passivation layer is a dielectric material deposited using CVD processes and may be silicon oxide, silicon nitride, or other commonly used passivation material. FIG. 4 is a cross-sectional view of a portion of partially fabricated BioFET device 400 after operation 206 of FIG. 2. The BioFET device 400 includes a passivation layer 401 over a top metal layer 403 having metal plates 405, 407, 409, and 411 and an underlying metal layer 413 having conductive vias (metal vias) 415 and conductive lines 417. The metal plates 405, 407, 409, and 411 include one or more liners. Liner 419 may be an adhesion layer or an etch stop layer formed of a conductive material, for example, titanium or titanium nitride. Liner 421 may be a dielectric material that is at least partially removed between metal features to allow signal conduction. Liner 421 may be an anti-reflection coating, for example, silicon oxynitride.

Figure 5:
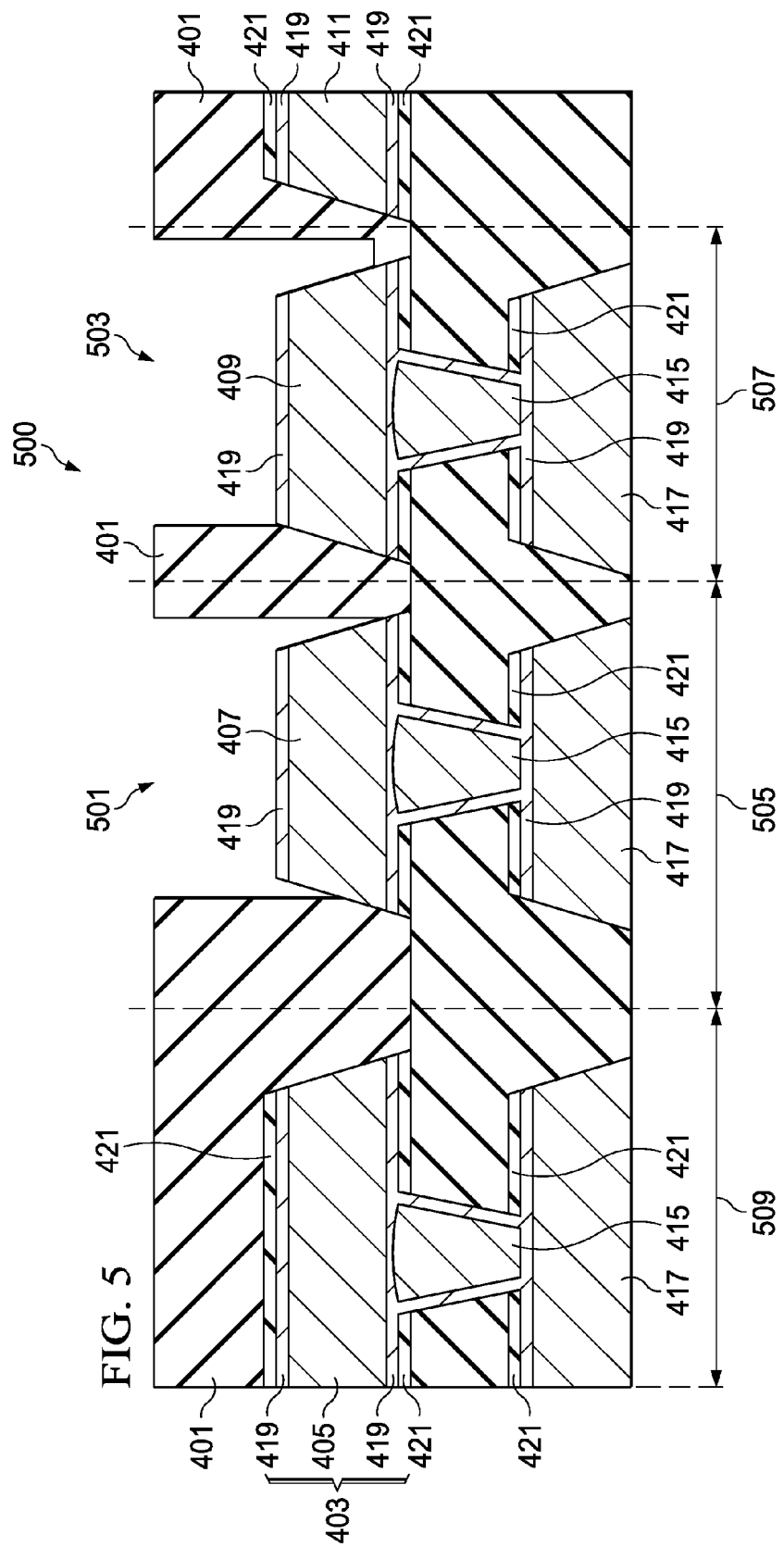

Referring back to FIG. 2, in operation 208 microwells are etched in the passivation layer to expose some top metal plates. A layer of photoresist is patterned to a width that about the same as a top width of the metal plate or larger than the top width of the metal plate. Using the patterned photoresist as an etch mask, openings are etched in the passivation layer to expose some metal plates. The exposed metal plates are those connected to the BioFETs. The etch process may be a wet etch or a dry etch. FIG. 5 is a cross-sectional view of a portion of partially fabricated BioFET device 500 after operation 208. Openings 501 and 503 are etched in the passivation layer 401 to expose metal plates 407 and 409, respectively. The BioFET device 500 is separated into different regions 505, 507, and 509 to show different processing scenarios. Region 505 includes an opening 501 that is aligned with the metal plate 407. Liner material on the top metal plate is removed during the etch process. Some passivation material 401 from the top metal layer 403 adjacent to the metal plate 407 may also be removed during the etch process. Region 507 includes an opening 503 that is not perfectly aligned with the metal plate 409. As result, the opening exposes sidewall of the metal plate 409 only on one side. Additional passivation material 401 is also removed from one side of the metal plate 409. However, the dimensions of the opening is such that such misalignment does not cause the opening to expose adjacent metal plate 411. The metal plate 405 in region 509 is not exposed by an opening.

Referring back to FIG. 2, in operation 210 the exposed top metal plates are removed. A selective metal etching process is used to preferentially remove the top metal plate material over the surrounding passivation layer 401. The liner 421 under the exposed metal plate acts as an etch stop layer and is not substantially removed. Because only the exposed top metal plate is removed, the process forms self-aligned microwells with definite borders. In some embodiments, the selective metal etching process is a wet etch. The etchant may be an acid that selectively etches the material of the top metal plate over the material of the underlying etch stop layer. The etchant may be M2 acid (a mixture of phosphoric acid, nitric acid, and acetic acid), dilute hydrofluoric acid, hydrochloric acid or another acid having a desired etch selectivity. In other embodiments, the selective metal etch process is a dry etch using reactive ions to remove the top metal plate. The dry etch may use a chlorine based or a fluorine based etchant in a plasma process. The dry etch process may include a soft landing etch that ensures that the underlying material is not removed unnecessarily. In some embodiments, the soft landing etch is performed using little or no bias power and low energy plasma or no plasma and stops when an etch stop condition is detected. Process conditions during the etch is monitored and when a parameter changes corresponding to an etched material property change, for example, detecting the presence of liner material. When used with a slow etch process, the end point detection can stop the etch accurately and minimized plasma-induced damage to the liner.

Figure 6:
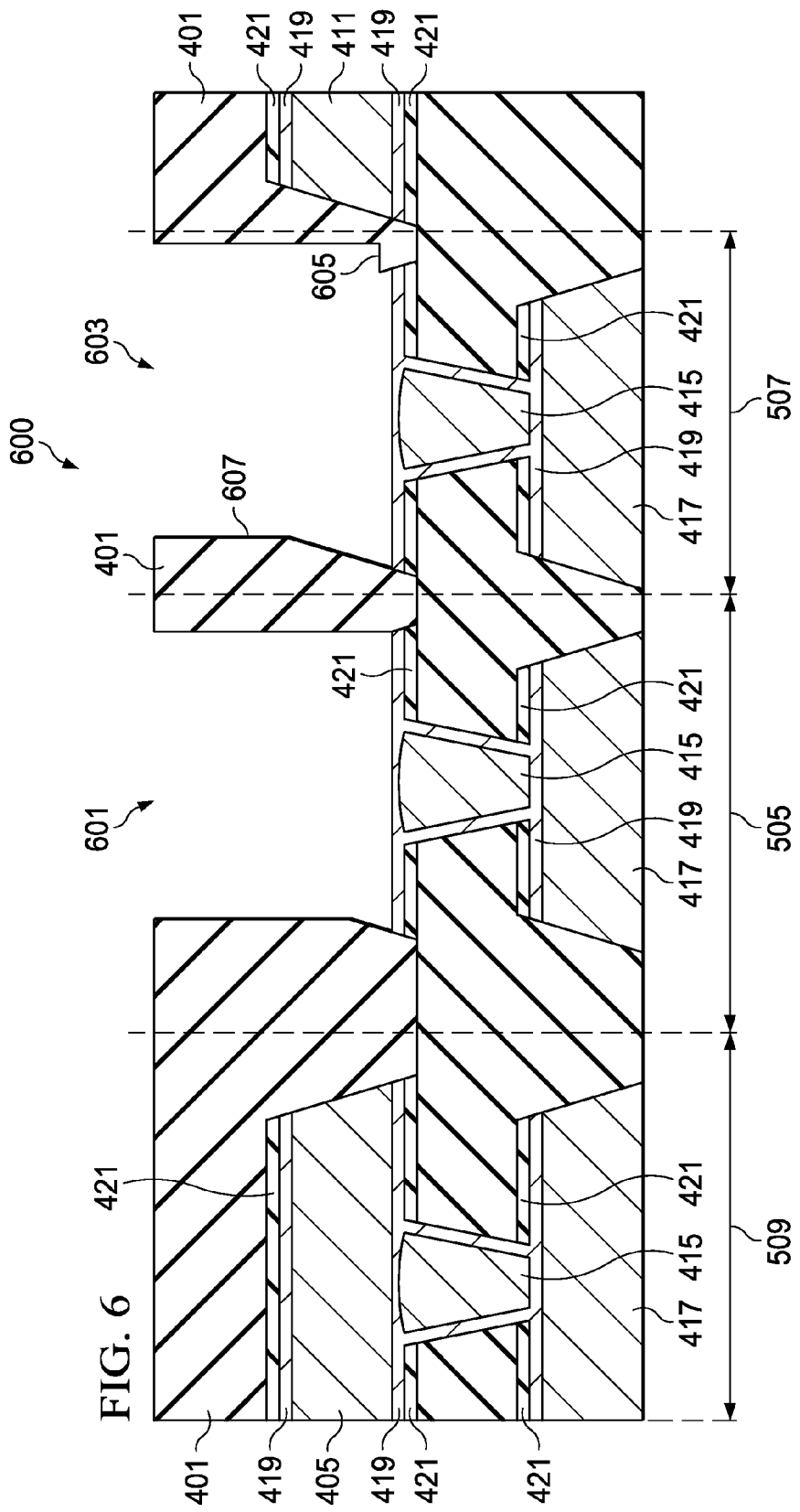

FIG. 6 is a cross-sectional view of a portion of BioFET device 600 after operation 210. In region 505, the selective metal etch forms a microwell 601 having the conductive liner 421 at the bottom and sidewalls that have substantially equal profiles. In region 507, the selective metal etch forms a microwell 603 having the conductive liner 421 at the bottom and sidewalls that have different profiles. Where the misalignment of the opening from operation 208 is offset into the passivation 401, the sidewall 605 has a step, corner, or shelf An opposing sidewall 607 has a profile that is the same as the sidewall of the removed top metal plate. Microwells 601 and 603 are deeper than microwells formed over the top metal plate by having an additional depth equal to the thickness of the top metal plate. As result the surface area inside the microwells 601 and 603 for a bio-sensing layer is greater. Further, removing the top metal plates avoids the crack corrosion issues and signal bridging issues as discussed. The microwell formation of operations 208 and 210 is less sensitive to misalignment.

Figure 7:
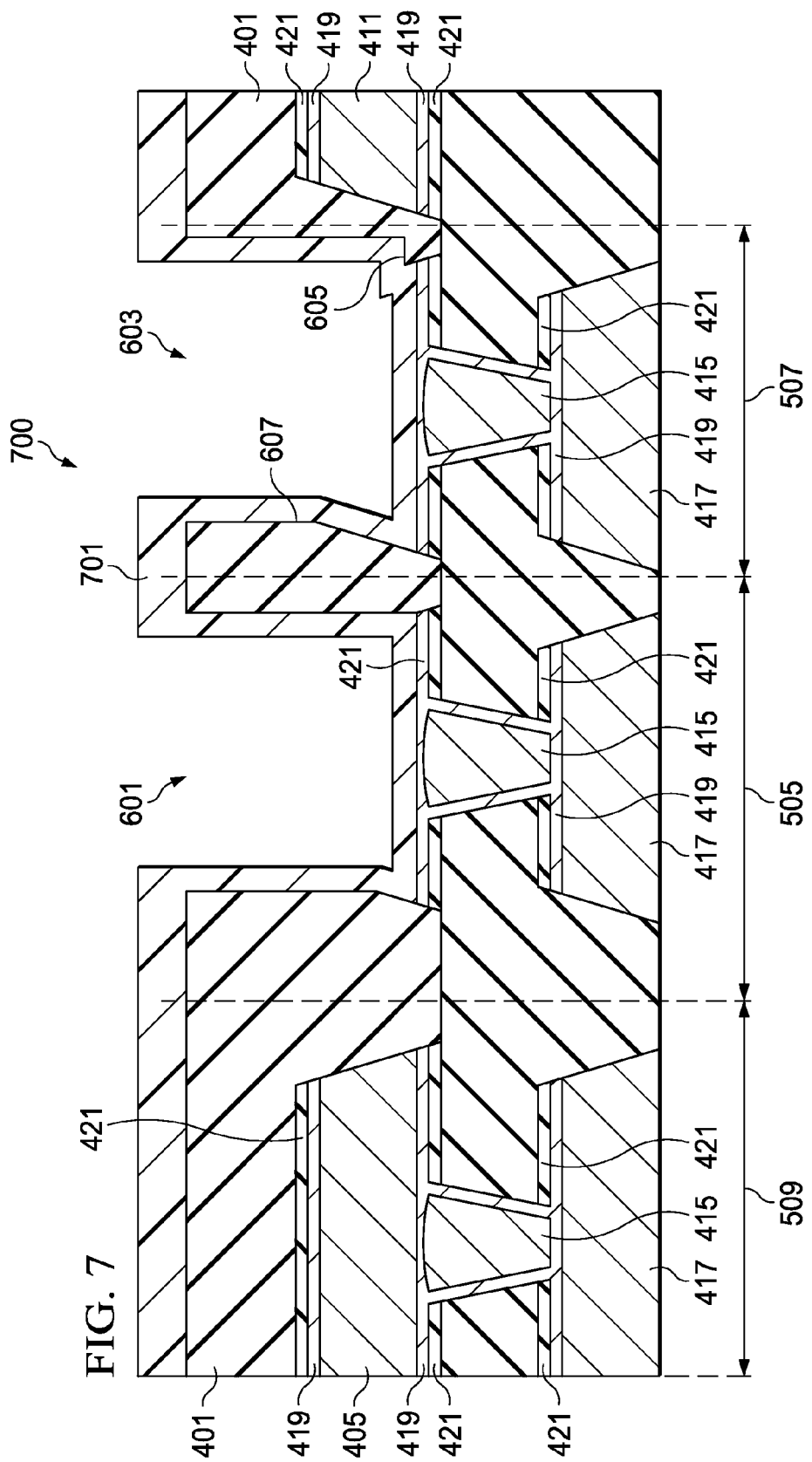

Referring back to FIG. 2, in operation 212 a bio-sensing layer is deposited in the microwells and over a field between the microwells. The bio-sensing layer is deposited using spin-on coating, CVD or PVD processes having good coverage for the sidewalls of the microwells. In some embodiments, an atomic layer deposition (ALD) process is used to conformally coat the bottom and sidewalls of the microwells and the field between the microwells. The deposition process is selected so that even entrenched sidewall profiles can be conformally coated. The bio-sensing layer may be titanium nitride, tungsten, a high-k dielectric such as aluminum oxide, lanthanum oxide, hafnium oxide, and tantalum oxide, self-assembled monolayer, or hydrogel. The bio-sensing layer is deposited to a sufficient thickness so that electrical signals representing conditions of the analyte in the microwells can be transmitted to the gate below. The bio-sensing layer may bind directly to biomolecules in the test sample or indirectly through a surface treatment or a bioreceptors. FIG. 7 is a cross-sectional view of a portion of BioFET device 700 after operation 212. A bio-sensing layer 701 is deposited over the wafer and in the microwells 601 and 603. Depending on the deposition process, the bio-sensing layer may not have uniform thickness in the field portion between microwells and the sidewalls in the microwells. Complete sidewall coverage ensures that more binding sites are available on the bio-sensing layer for the biomolecules.

Referring back to FIG. 2, in operation 214 at least the field portion of the bio-sensing layer is removed. Removing the field portion of the bio-sensing layer isolates the bio-sensing layer for different BioFETs from each other and prevents signal cross talk. Operation 214 includes a number of steps. A photoresist layer is deposited on the wafer and planarized. The photoresist is then patterned to form openings to expose bio-sensing layer on field areas between the microwells. Exposed bio-sensing layer is removed from field areas depending on the material. For certain metal bio-sensing layers, for example, titanium nitride, a selective metal etch is performed to remove the bio-sensing layer on the field areas. For other bio-sensing layers, for example, tungsten or hydrogel, a chemical mechanical polishing (CMP) process is used. Any remaining photoresist in the microwells is removed by ashing. In some embodiments, the photoresist for operation 214 has an opposite exposure from the photoresist for operation 208. Using the opposite exposure photoresist allows the same photomask to be used for both operations.

Figure 8:
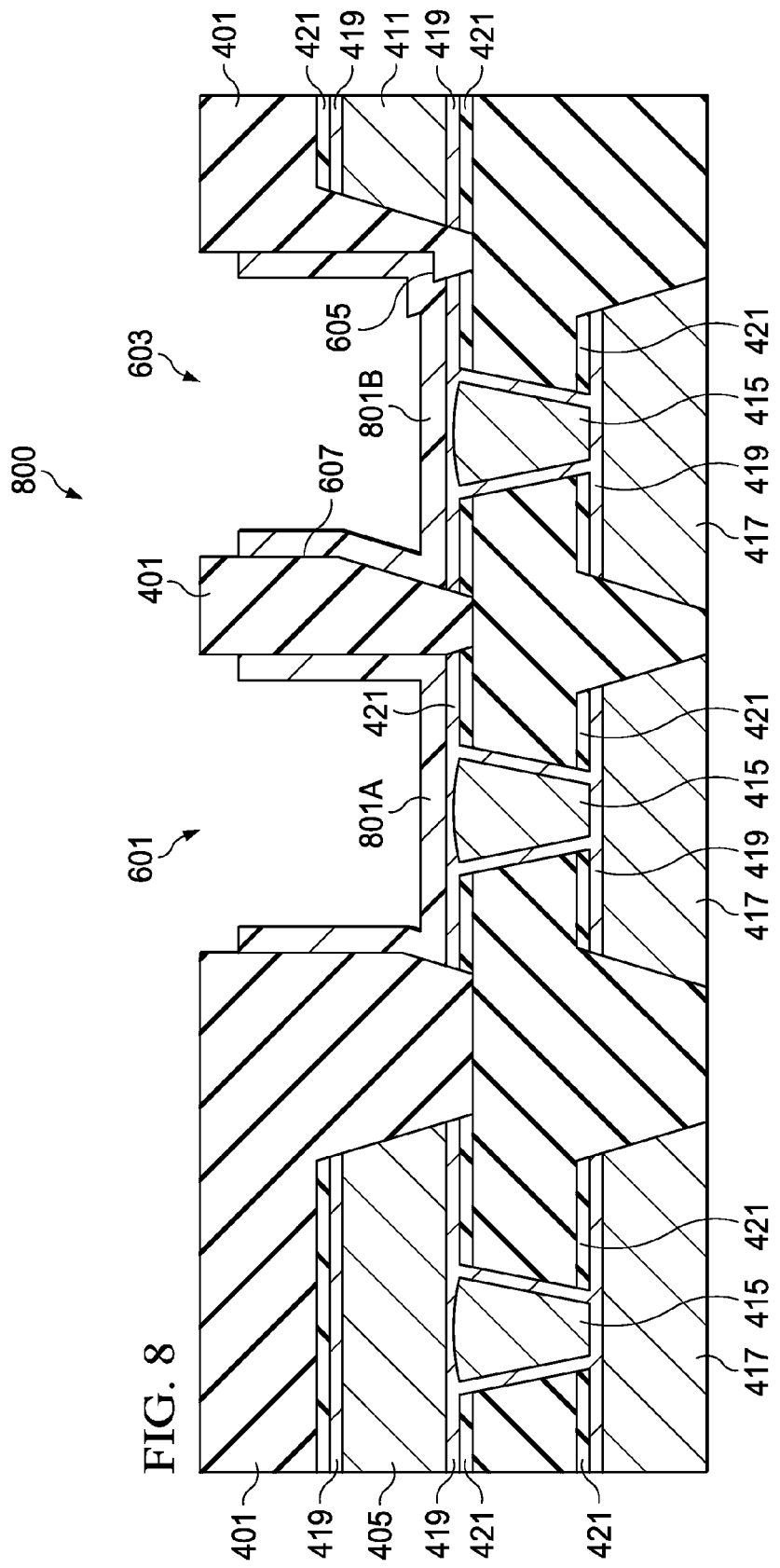

FIG. 8 is a cross-sectional view of a portion of BioFET device 800 after operation 214. Bio-sensing layers 801A and 801B covers the sidewalls and bottoms of microwells 601 and 603 are isolated from each other. As shown, a small edge portion of the bio-sensing layers 801A and 801B are removed from the lips of the microwells 601 and 603 by the selective metal etching process. When the photoresist is etched back, the corners of the microwells 601 and 603 are exposed, allowing a wet etchant to remove the bio-sensing layer from upper portions of the microwell sidewalls. In other embodiments, the bio-sensing layers 801A and 801B completely covers the sidewalls of the microwells 601 and 603. The photoresist may completely cover the edges of the sidewalls during a dry etch to remove the bio-sensing layer from the field areas. When a CMP process is used to remove the bio-sensing layer from the field areas, some bio-sensing layer from upper portions of the microwell sidewalls may also be removed.

Figure 9:
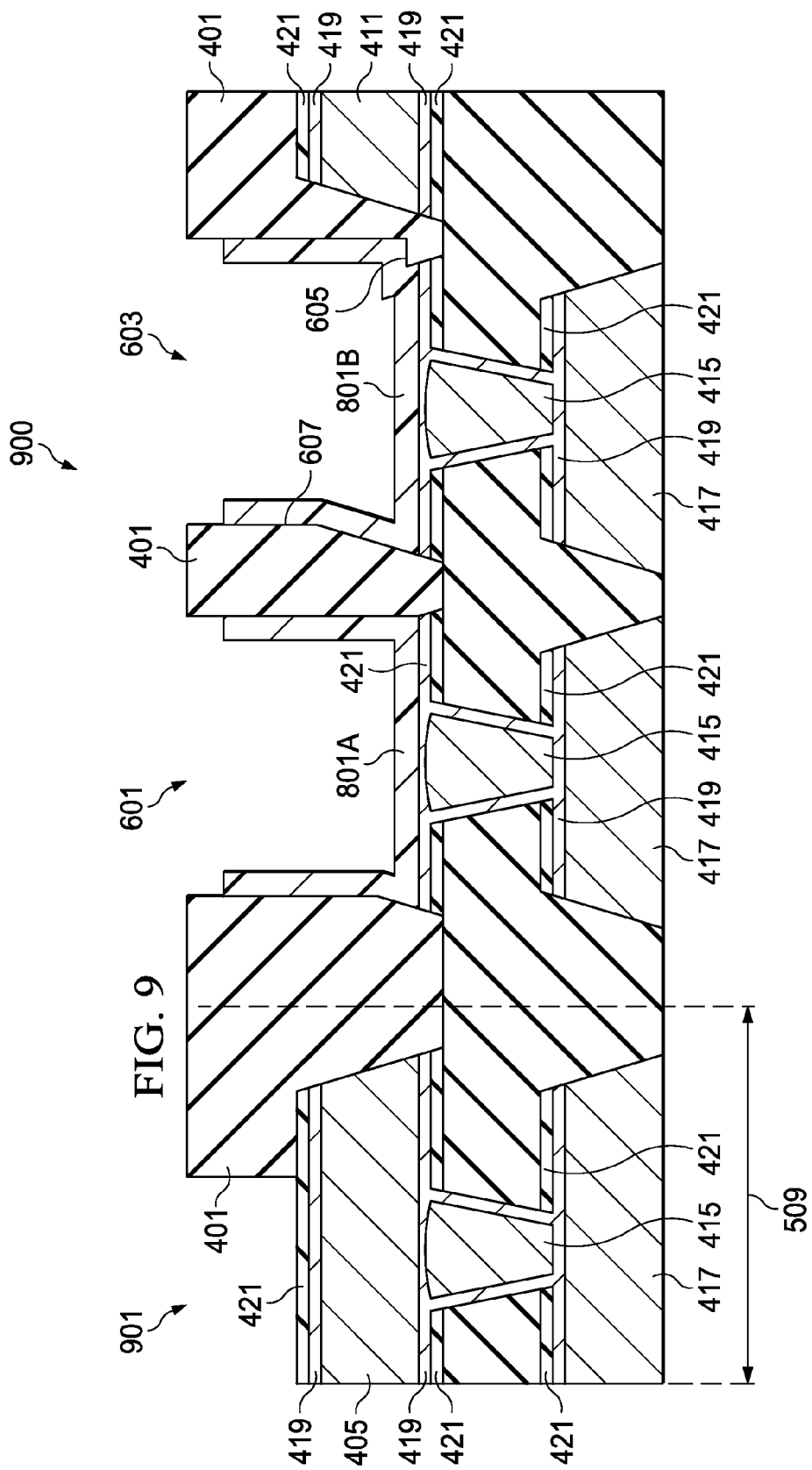

Referring back to FIG. 2, in optional operation 216, openings are formed to expose a second subset of the top metal plates. The second subset of the top metal plates is the bond pads used for externally connecting the BioFET device. In some embodiments, wires are bonded to the bond pads to transmit power and signal. In other embodiments, conductive members such as bumps and pillars are used to externally connect the BioFET device. The opening is formed by first depositing and patterning a photoresist layer over the wafer and etching through the pattern. FIG. 9 is a cross-sectional view of a portion of BioFET device 900 after operation 216. Opening 901 is formed in region 509 to expose top metal plate 405 as a bond pad. In some embodiments, the operations 214 and 216 may be partially combined to reduce the number of processes. For example, photoresist material in the microwells 601 and 603 may be ashed with the photoresist material from operation 216.

Referring back to FIG. 2, in optional operation 218, the bio-sensing layer surface may be treated. The treatment may include depositing a chemical to render the surface hydrophilic or hydrophobic. In some cases, the treatment may modify the surface to have certain conductance or magnetic properties. The treatment may also include labeling, or functionalizing, the bio-sensing layer with certain chemicals or biomolecules as receptors. The receptors may be enzyme, antibody, ligand, peptide, nucleotide, cell of an organ, organism or piece of tissue is provided or bound on the bio-sensing layer for detection of a target biomolecule. For instance, to detect ssDNA (single-stranded deoxyribonucleic acid), the sensing film may be functionalized with immobilized complementary ssDNA strands. Also, to detect various proteins such as tumor markers, the sensing film may be functionalized with monoclonal antibodies. The receptors may be a part of self-assembled monolayer (SAM) of molecules. The SAM may have head groups of silane groups, silyl groups, silanol groups, phosphonate groups, amine groups, thiol groups, alkyl groups, alkene groups, alkyne groups, azido groups, or expoxy groups. The receptors are attached to the head groups of SAM.

In some embodiments, BioFET device includes a microfluidic structure over the microwells. The microfluidic structures may include micropumps and valves and magnetic material or ferromagnetic material for magnetophoresis, metals for electrophoresis, electro wetting on dielectric (EWOD) or particular dielectric material for dielectrophoresis. The microfluidic structure may also electrically connect to the various bond pads adjacent to the microwells. The microfluidic structure has a bottom that seals the field area between adjacent microwells and provides channels for flowing reagents and test samples. The microfluidic structure may be transparent or partially transparent to allow observation of the reactions. In other embodiments, the microwells on the BioFET device is accessed from the top without a cover. Microfluidic channels may be formed directly in the passivation layer.

Figure 10A:
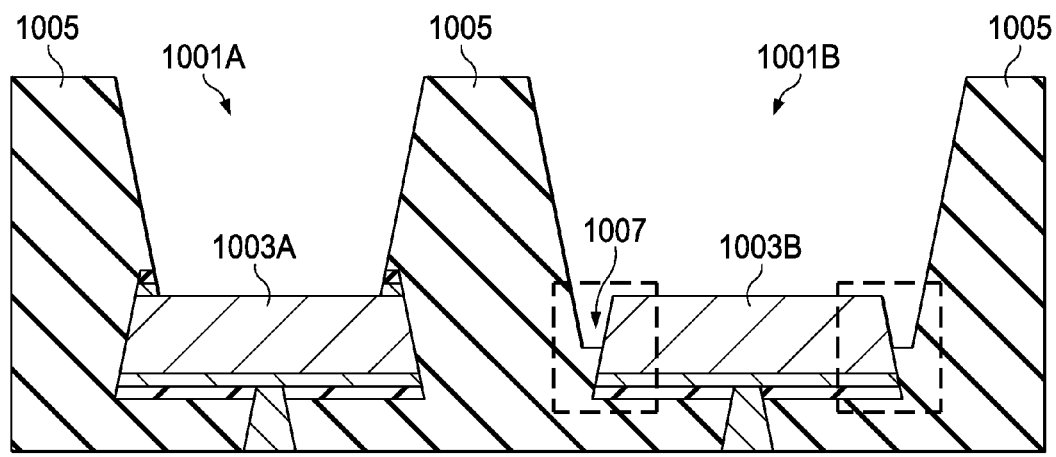
FIGS. 10A-10D are cross-sectional views of a BioFET device having aligned microwells at various intermediate stages of formation according to one or more aspects of the present disclosure.

FIGS. 10A-10D are cross-sectional views of a portion of BioFET device having aligned microwells at various intermediate stages of formation according to one or more aspects of the present disclosure. The left portions of FIGS. 10A-10D represent a scenario where a bottom surface area of a top portion of the microwell is smaller than a top surface of a bottom portion of the microwell. In other words, the microwell etching operation 208 of FIG. 2 is performed with a pattern that is smaller than the top plate width. The right portions of FIGS. 10A-10D represent a scenario where a bottom surface area of a top portion of the microwell is larger than a top surface of a bottom portion of the microwell. In other words, the microwell etching operation 208 of FIG. 2 is performed with a pattern that is larger than the top plate width. FIG. 10A is the cross section after operation 208. The bottom surface of the opening 1001A is exposed portions of the top metal plate 1003A. The bottom surface of the opening 1001B includes not only exposed portion of the top metal plate 1003B, but also a portion of the sidewalls of the top metal plate 1003B and passivation layer 1005 adjacent to the top metal plate 1003B. The bottom surface of the opening 1001B includes a shelf 1007.

Figure 10B:
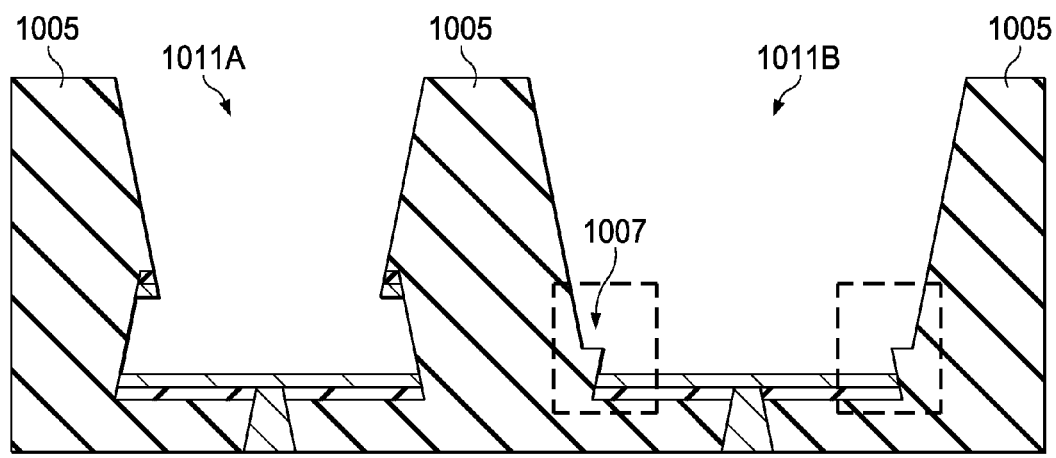
Figure 10C:
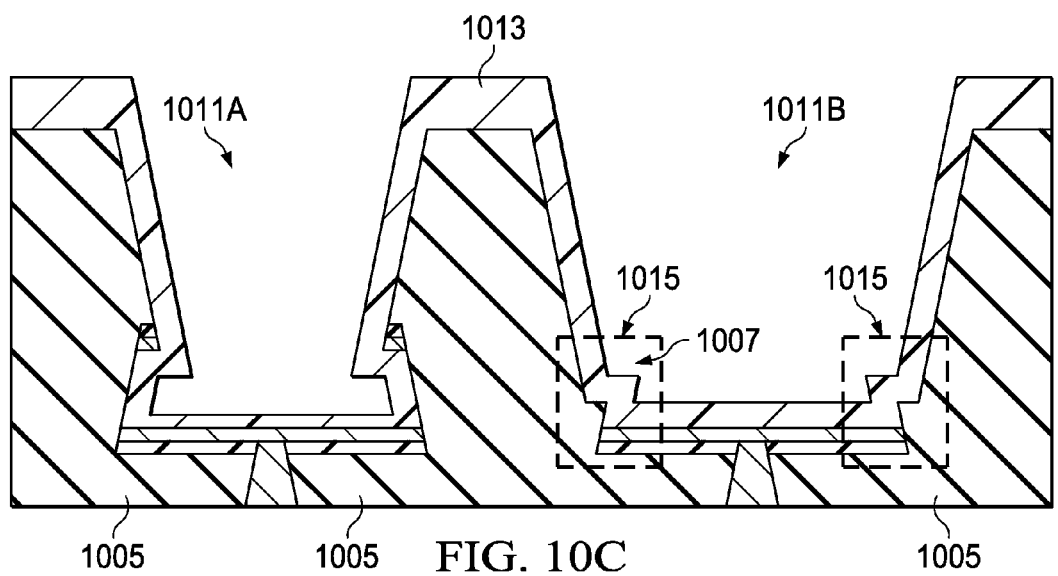
Figure 10D:
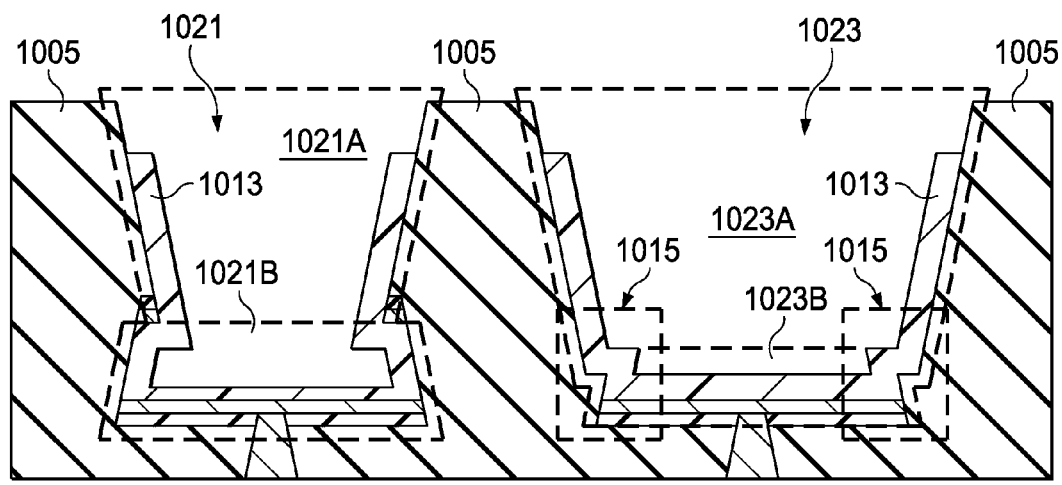

FIG. 10B is the cross section after operation 210 of FIG. 2 where the top metal plates are removed. A retrenched opening 1011A is formed after removing the top metal plate 1003A. The shelf 1007 remains in the opening 1011B after the top metal plate 1003B is removed. FIG. 10C is the cross section after operation 212 of FIG. 2 after the bio-sensing layer is deposited. The conformal bio-sensing layer 1013 covers the microwell sidewalls including under the retrenched portions in microwell 1011A. In microwell 1011B, the conformal bio-sensing layer also forms a shelf profile as shown in dotted line box 1015. FIG. 10D is the cross section after operation 214 of FIG. 2. The microwell 1021 includes two portions 1021A and 1021B. The top portion 1021A has a bottom surface area that is smaller than a top surface area than the bottom portion 1021B. The microwell 1023 includes two portions 1023A and 1023B. The top portion 1021A has a bottom surface area that is larger than a top surface area than the bottom portion 1021B.

FIGS. 11A-11D are cross-sectional views of a portion of BioFET device having misaligned microwells at various intermediate stages of formation according to one or more aspects of the present disclosure. The left portions of FIGS. 11A-11D represent a scenario where a bottom surface area of a top portion of the microwell is smaller than a top surface of a bottom portion of the microwell. In other words, the microwell etching operation 208 of FIG. 2 is performed with a pattern that is smaller than the top plate width. The right portions of FIGS. 11A-11D represent a scenario where a bottom surface area of a top portion of the microwell is larger than a top surface of a bottom portion of the microwell. In other words, the microwell etching operation 208 of FIG. 2 is performed with a pattern that is larger than the top plate width. The bottom surface of the opening 1101A is exposed portions of the top metal plate 1103A and a portion of the sidewall of the top metal plate 1103A. The bottom surface of the opening 1101B includes not only exposed portion of the top metal plate 1103B, but also a portion of the sidewalls of the top metal plate 1103B and passivation layer 1105 adjacent to the top metal plate 1103B. The bottom surface of the opening 1101B includes a shelf 1107.

Figure 11A:
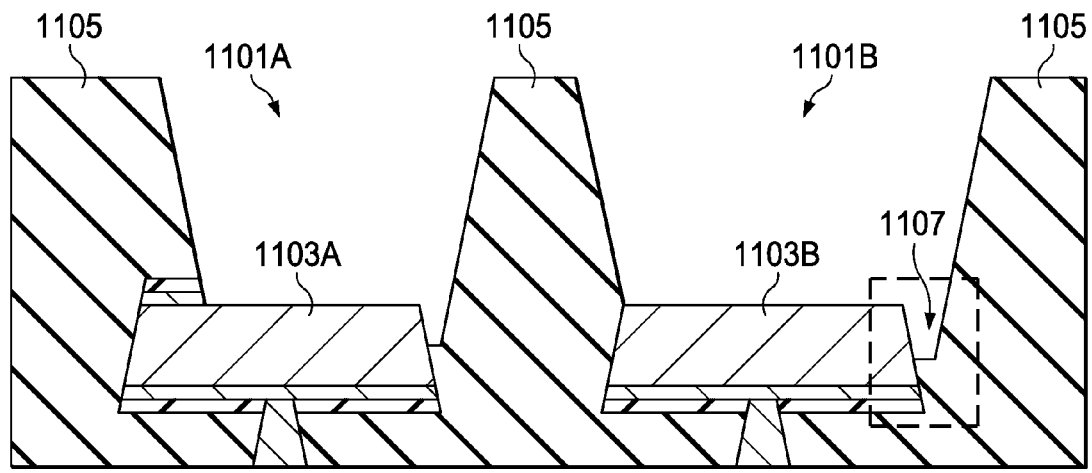
FIGS. 11A-11D are cross-sectional views of a BioFET device having misaligned microwells at various intermediate stages of formation according to one or more aspects of the present disclosure.
Figure 11B:
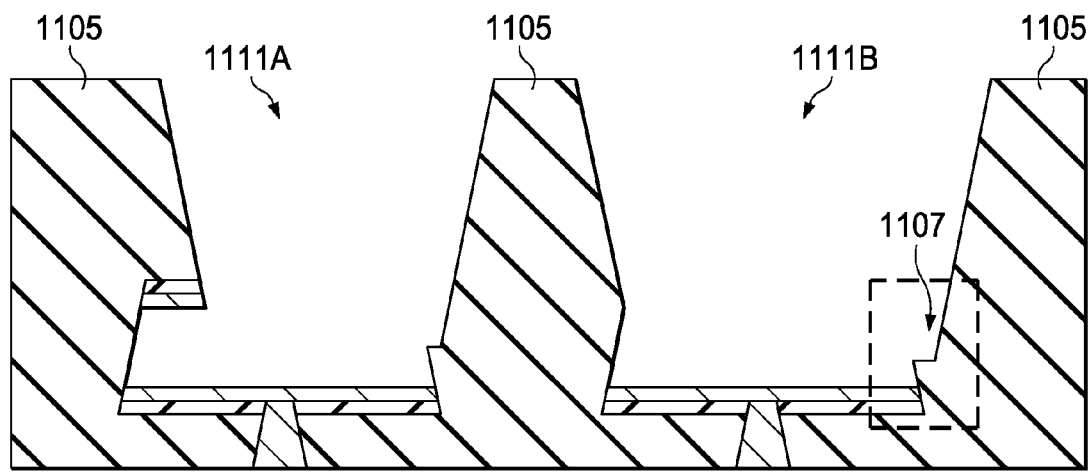
Figure 11C:
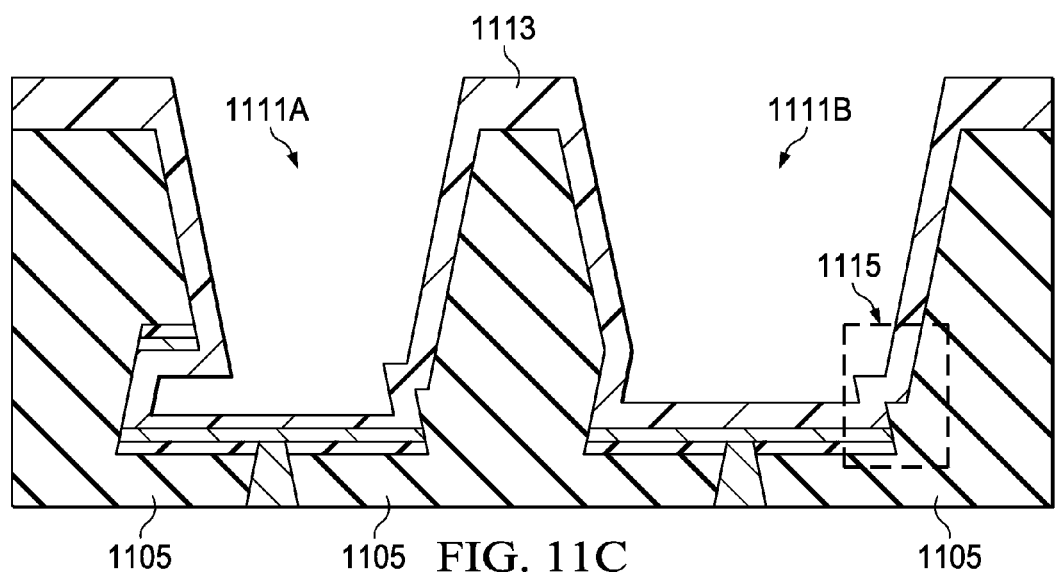
Figure 11D:
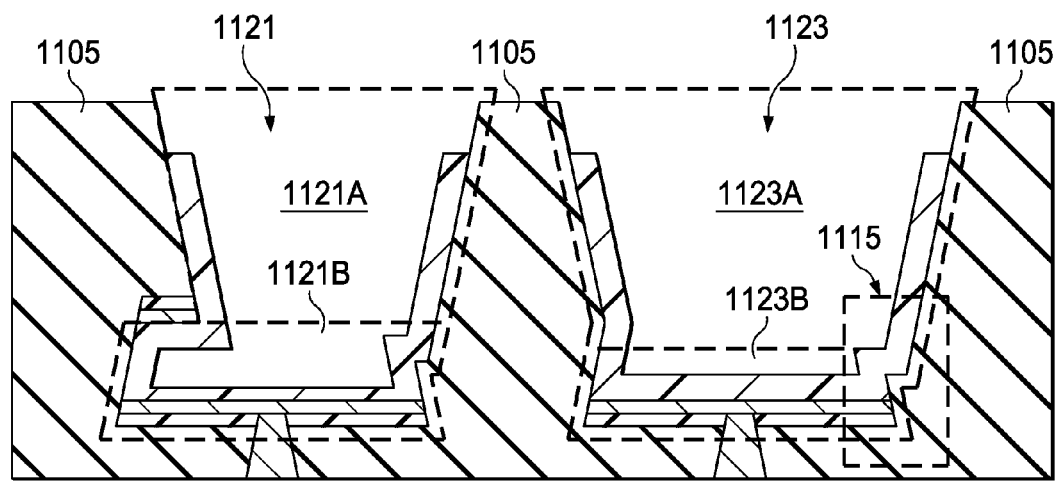

FIG. 11B is the cross section after operation 210 of FIG. 2 where the top metal plates are removed. A retrenched opening 1111A on one side is formed after removing the top metal plate 1103A. The shelf 1107 remains in the opening 1111B after the top metal plate 1103B is removed. The profiles of sidewalls in opposite sides of openings 1111A and 111lB are different. FIG. 11C is the cross section after operation 212 of FIG. 2 after the bio-sensing layer is deposited. The conformal bio-sensing layer 1113 covers the microwell sidewalls including under the retrenched portions in microwell 1111A. In microwell 1111B, the conformal bio-sensing layer also forms a shelf profile as shown in dotted line box 1115. FIG. 11D is the cross section after operation 214 of FIG. 2. The microwell 1121 includes two portions 1121A and 1121B. The top portion 1121A has a bottom surface area that is smaller than a top surface area than the bottom portion 1121B. The microwell 1123 includes two portions 1123A and 1123B. The top portion 1121A has a bottom surface area that is larger than a top surface area than the bottom portion 1121B. As shown in FIG. 11D, the top portion and bottom portion of a microwell may be different sizes.

FIG. 3 is a flow chart of an embodiment of a method 300 of using a BioFET device according to one or more aspects of the present disclosure. In operation 302, a BioFET device is received. The BioFET device is as described in various embodiments of the present disclosure. The BioFET device has a plurality of microwells having a top well portion and a bottom well portion, wherein a bottom surface area of the top well portion is different from a top surface area of the bottom well portion. The BioFET device also includes a multi-layer interconnect (MLI) connecting a bottom of each of the plurality of microwells to one or more transistor gates. In optional operation 304, a surface of the microwells is treated. In some embodiments, the BioFET device is received with the treatment already performed. In other embodiments, the treatment is performed before after receipt of the BioFET device. The treatment operation is similar to that described in associate with operation 218 of FIG. 2.

In operation 306 of method 300, a test sample is loaded in the BioFET device. The test sample may be in a carrier medium. In some embodiments, the test sample is bound to a carrier bead. In other embodiments, the test sample is suspended in a fluidic medium. The loading operation flows the test sample to various microwells where they are bound directly or indirectly to the bio-sensing layer.

In operation 308, a reagent is flowed in the BioFET device to the microwells. The reagent reacts with some or all of the test samples in the microwells. The existence of reaction or the extent of the reaction is recorded by measuring the current through the source and drain of the BioFET in operation 310. Several measurements of the current may be made at different times. For example, a blank measurement may be made to establish the baseline with deionized water. Another measurement may be made after the test sample is loaded to establish a second baseline. One or more measurements may be made to record the change in current during the reagent flow and residence in the BioFET device. In some embodiments, FET devices operate in linear region for detection. In some embodiments, FET device operate in saturation region for detection.

In operation 312, the measurement is analyzed. The measurement may be outputted by the BioFET device to a computer or a processor to analyze the signals. In some embodiments, an analog signal is first converted to a digital signal. The data may be analyzed by a processor running a software program or by a user. In some embodiments, the measurement is analyzed on board the BioFET device.

The BioFET device may be a single use or a multiple use device. In optional operation 314, the BioFET device is flushed to remove the reagent from the microwells and operations 308 to 312 repeated with a second reagent. The test sample remains in the BioFET device as different reagents are cycled through. This process may be used to identify an unknown substance. By recording reactions using different reagents, the identity of an unknown substance may be narrowed down. This process may be used to perform DNA sequencing. For example, a test sample of strands of DNA may be loaded into BioFET device. The strands may be amplified in each microwell to form a colony. By sequentially adding reagents containing different nucleobases and measuring reactions in each microwell, the identity of the strand in each microwell may be found.

In one aspect, the present disclosure pertains to a biological field-effect transistor (BioFET) device that includes a substrate and a number of BioFETs. The BioFET includes a microwell having a top well portion and a bottom well portion, a number of metal layers under the microwell, and one or more transistors having a gate of the one or more transistors connected to the plurality of metal layers under the plurality of metal layers. A bottom surface area of the top well portion is different from a top surface area of the bottom well portion. Each of the plurality of metal layers includes a metal plate and at least one metal via. A metal via in a topmost layer of the plurality of metal layers is directly connected to the microwell.

In another aspect, the present disclosure pertains to a method of forming a BioFET device. The method includes forming a plurality of FETs on a semiconductor substrate, forming a gate contact on a gate in each of the plurality of FETs, forming a multi-layer interconnect (MLI) over the plurality of FETs, and forming a passivation layer over the MLI. The MLI includes a top metal layer having a plurality of metal plates. The method also includes etching microwells in the passivation layer to expose a subset of the plurality of top metal plates, removing the exposed top metal plates, depositing a bio-sensing layer in the microwells and over a field between the microwells, and removing at least the field portion of the bio-sensing layer.

In yet another aspect, the present disclosure pertains to a method of sensing bio-reactions. The method includes receiving a BioFET device as disclosed in the present disclosure, loading a test sample in the BioFET device, flowing a reagent in the BioFET device to the plurality of microwells, measuring a change in a transistor current corresponding to each of the plurality of microwells, and analyzing the measurement.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A method of making a biological field-effect transistor (BioFET) device, comprising:
    forming a plurality of field-effect transistors (FETs) on a semiconductor substrate, wherein the plurality of FETs each includes a gate structure formed on a first surface of the semiconductor substrate and a channel region;
    forming a gate contact on the gate structure in each of the plurality of FETs;
    forming a multi-layer interconnect (MLI) over the plurality of FETs, wherein the MLI includes a top metal layer having a plurality of top metal plates;
    forming a passivation layer over the MLI;
    etching microwells in the passivation layer to expose a subset of the plurality of top metal plates;
    removing the exposed top metal plates;
    depositing a bio-sensing layer in the microwells and over a field portion between the microwells; and
    removing at least the field portion of the bio-sensing layer.

2. The method of claim 1, further comprising:
    forming an opening over a second subset of the plurality of top metal plates.

3. The method of claim 1, wherein the removing the exposed top metal plates comprises:
    selectively wet etching the exposed top metal plates.

4. The method of claim 1, further comprising:
treating the bio-sensing layer surface.

5. The method of claim 1, wherein the removing at least the field portion of the bio-sensing layer comprises:
depositing a photoresist layer;
planarizing the photoresist layer;
etching back the planarized photoresist layer;
etching exposed portions of the bio-sensing layer; and
removing a remaining portion of the photoresist layer in the microwells.

6. The method of claim 5, wherein the etching exposed portion of the bio-sensing layer comprises a chemical mechanical polishing process or grinding process.

7. The method of claim 1, wherein the step of etching microwells in the passivation layer to expose a subset of the plurality of top metal plates includes exposing respective first sidewalls of the plurality of top metal plates while leaving unexposed respective second sidewalls of the plurality of top metal plates.

8. The method of claim 2, further comprising forming electrical connectors on respective ones of the second subset of the plurality of top metal plates.

9. A method of making a biological field-effect transistor (BioFET) device, comprising:
forming a transistor on a semiconductor substrate;
forming a multi-layer interconnect (MLI) over the transistor, wherein the MLI includes at least one top metal plate electrically connected to the transistor;
depositing a passivation layer over the MLI;
etching an opening in the passivation layer to expose the at least one top metal plate;
removing the exposed at least one top metal plate to form a microwell, the microwell having a top portion with a shape of the opening and a bottom portion with a shape of the at least one top metal plate; and
depositing a bio-sensing layer in the microwell.

10. The method of claim 9, wherein the step of depositing a bio-sensing layer in the microwell comprises:
depositing the bio-sensing layer in the microwell and over a top surface of the passivation layer; and
removing at least a portion of the bio-sensing layer on the top surface of the passivation layer.

11. The method of claim 10, wherein the step of removing at least a portion of the bio-sensing layer on the top surface of the passivation layer includes removing a portion of the bio-sensing layer from an upper region of the microwell.

12. The method of claim 9, wherein the step of etching an opening in the passivation layer to expose the at least one top metal plate exposes a first sidewall of the at least one top metal plate while leaving unexposed a second sidewall of the at least one top metal plate.

13. The method of claim 9, further comprising:
depositing a photoresist layer over the deposited bio-sensing layer;
planarizing the photoresist layer;
etching back the planarized photoresist layer;
etching exposed portions of the bio-sensing layer; and,
removing a remaining portion of the photoresist layer in the microwells.

14. A method of making a biological field-effect transistor (BioFET) device, comprising:
forming a first transistor and a second transistor on a substrate;
forming a multi-layer interconnect (Mil) over the first and the second transistors, wherein a top layer of the Mil comprises a first top metal plate and a second top metal plate, with the first top metal plate electrically coupled to the first transistor, and the second top metal plate electrically coupled to the second transistor;
depositing a dielectric layer over the Mil;
forming a top opening in the dielectric layer, the top opening exposing the first top metal plate;
removing the first top metal plate to form a bottom opening under the top opening, the top opening and the bottom opening forming a well; and
depositing a bio-sensing layer in the well.

15. The method of claim 14, further comprising:
forming another top opening in the dielectric layer, the another top opening exposing the second top metal plate; and
making an electrical connection to the second top metal plate.

16. The method of claim 15, further comprising covering the well before forming the another top opening.

17. The method of claim 14, wherein the depositing the bio-sensing layer comprises:
depositing the bio-sensing layer on a bottom and sidewalls of the well.

18. The method of claim 14, wherein the first top metal plate is electrically coupled to a first gate structure of the first transistor, and the second top metal plate is electrically coupled to a second gate structure of the second transistor.

19. The method of claim 14, wherein the step of forming a top opening in the dielectric layer exposes a first sloped sidewall of the first top metal plate and does not expose a second sloped sidewall of the first top metal plate.

20. The method of claim 14, wherein the top opening has first sidewalls and the bottom opening has second sidewalls, the first sidewalls and the second sidewalls being continuous, at least one second sidewall minoring a corresponding sidewall of the first top metal plate.

* * * * *

UNITED STATES PATENT AND TRADEMARK OFFICE
CERTIFICATE OF CORRECTION

Page 1 of 1

PATENT NO.        : 9,228,974 B2
APPLICATION NO.   : 13/946782
DATED             : January 5, 2016
INVENTOR(S)       : Yi-Hsien Chang It is certified that error appears in the above-identified patent and that said Letters Patent is hereby corrected as shown below:

Claims

In Col. 14, line 13, claim 14, delete "(Mil)" and insert --(MLI)--.

In Col. 14, line 14, claim 14, delete "Mil" and insert --MLI--.

In Col. 14, line 19, claim 14, delete "Mil;" and insert --MLI;--.

In Col. 14, line 49, claim 20, delete "minoring" and insert --mirroring--.

Signed and Sealed this
Nineteenth Day of April, 2016

Michelle K. Lee
*Director of the United States Patent and Trademark Office*